US00PP33126P3

(12) United States Plant Patent
Hansoti

(10) Patent No.: US PP33,126 P3
(45) Date of Patent: Jun. 1, 2021

(54) ***SANSEVIERIA* 'HANSOTI22'**

(50) Latin Name: *Sansevieria trifasciata*
Varietal Denomination: HANSOTI22

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 17/010,312

(22) Filed: Sep. 2, 2020

(65) Prior Publication Data

US 2021/0068327 P1 Mar. 4, 2021

(30) Foreign Application Priority Data

Sep. 4, 2019 (QZ) ..... PBR 2019/2152

(51) Int. Cl.
*A01H 6/12* (2018.01)
*A01H 5/00* (2018.01)

(52) U.S. Cl.
USPC ..... Plt./382
CPC ..... *A01H 6/12* (2018.05)

(58) Field of Classification Search
USPC ..... Plt./382
See application file for complete search history.

(56) References Cited

PUBLICATIONS

PLUTO Plant Variety Database Dec. 15, 2015.p. 1.*

* cited by examiner

*Primary Examiner* — Annette H Para
(74) *Attorney, Agent, or Firm* — Cassandra Bright

(57) ABSTRACT

A new and distinct cultivar of *Sansevieria* plant named 'HANSOTI22' is disclosed, characterized by dark green foliage with a yellow margin and distinctive yellow-green central streaking. Foliage is arranged in attractive spiral rosettes with lowermost foliage occurring at obtuse angles from the center of the plant. The new cultivar is a compact "birds nest" type *Sansevieria* forming small plants, reaching about 12 to 15 cm in height at maturity. Plants require little water, having a moderate tolerance for drought, and are also tolerant of very wet conditions. The new variety is a *Sansevieria*, typically produced as an indoor ornamental plant.

6 Drawing Sheets

Latin name of the genus and species: *Sansevieria trifasciata.*

Variety denomination: 'HANSOTI22'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI22'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI22' was discovered and selected by the inventor, Ashish Hansoti, as a single, naturally occurring whole plant mutation within a planting of *Sansevieria trifasciata* 'Hahnii Jade Marginata', a non-patented Hahnii or 'Birds Nest' type of *Sansevieria*. The discovery was made at the inventor's nursery, in Village Vangani, District Thane, Maharashtra State in Western India. The inventor noted the unique plant for its particularly compact growth and wide leaves compared to the normal, common green *Sansevieria trifasciata* 'Hahnii' types. 'HANSOTI22' originated as a naturally-occurring mutation of the *Sansevieria* variety 'Hahnii Jade Marginata' (unpatented) selected in May 2010.

Asexual reproduction of the new *Sansevieria* cultivar by vegetative cuttings was first performed in August of 2011 at a commercial nursery in Village Vangani, District Thane, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI22', which in combination distinguish this *Sansevieria* as a new and distinct cultivar:

1. Vivid and distinct central broad band of longitudinal lighter creamy yellow streaks along leaf lamina between the creamy yellow borders on both side of the leaf.
2. Highly compact plant forming on average 10 leaves and reaching a height around 15 cm at three months of age.

Leaf width is quite variable and the strongest, healthiest plants have the widest leaves, as is true across all *Sansevieria trifasciata* cultivars known to the inventor. This variation means leaf width can be anything from 3.5 cm to 8 cm wide depending on season, growing conditions and plant vigour and plant age. Typically, the leaves are of medium width (6 cm average measured at the widest part of the mature leaf under good growing conditions) and lanceolate with a firm, waxy texture. The blades are thick & fleshy.

The new variety 'Hansoti22' is a variety of *Sansevieria* in the group denominated as "Birds Nest" or 'Hahnii' types based on its origin. The new variety presents an average of 10 leaves per plant when it reaches its maturity (about 3 months from rooted Liner) but over time it can grow and accumulate many more leaves and increase in overall height.

The new variety is moderately drought tolerant and adapts well to conditions of bright light or heavy shade (exterior and interior). The intensity of these central bands varies with exposure to light and the contrast is most intense under high light conditions.

The leaves show a variegated colouration, with a central wide area of darker green and a border of lighter yellowish-green. This central darker green area is longitudinally marked by a distinct band consisting of lighter creamy green streaks.

Each leaf has a marginal cream band similar to Yellow 4B and varies in width from just 2 mm to 10 mm. This creamy yellow border is occasionally invaded with streaks of darker green from the central dark green area. This characteristic is seen and is identical in its parental cultivar, 'Hahnii Jade Marginata'.

The central broad dark green area shows colouration similar to 139A. There are little or no transverse horizontal bands on the leaves (otherwise so typically seen in most *S. trifasciata* cultivars). The characteristic (and unique to 'Hansoti 22') light greenish to creamy yellow streaks are between N144C to N144D. The backside of the leaves has similar coloration except that the typical *S. trifasciata* transverse horizontal banding is visible, though indistinctly so.

The attached color pictures are a better guide to the overall coloration and pattern. The primary distinctive characteristic is the lighter longitudinal band consisting of light greenish to creamy yellow streaks within the broad darker green central area

COMMERCIAL COMPARATOR

Plants of the new *Sansevieria* 'HANSOTI22' can be compared to the unpatented commercial variety 'Hahnii Jade'. Plants of the new *Sansevieria* 'HANSOTI22' differ from plants of this comparator according to the characteristics described in Table 1.

TABLE 1

Commercial Comparison

| | Characteristic | Comparator 'Hahnii Jade' | 'HANSOTI22' |
|---|---|---|---|
| 1. | Leaf size | 9 to 13 cm | 9 to 13 cm |
| 2. | Quantity of Leaves | 10 to 12 | 10 to 13 |
| 3. | Variegation Pattern | Dark green leaves. | Dark green leaves with a cream border and wide central band of light green/creamy yellow streaks |

PARENTAL COMPARISON

Plants of the new *Sansevieria* 'HANSOTI22' differ from plants of the parental cultivar in the characteristics described in Table 2.

TABLE 2

Comparison of New and Parental variety

| | Characteristic | Parent 'Hahnii Jade Marginata' | 'HANSOTI22' |
|---|---|---|---|
| 1. | Leaf size | 9 to 13 cm | 9 to 13 cm |
| 2. | Quantity of Leaves | 10 to 12 | 10 to 13 |
| 3. | Variegation Pattern | Dark green leaves with a cream border. | Dark green leaves with a cream border and wide central band of light green/creamy yellow streaks |
| 4. | Thickness of marginal variegation | 2 to 12 mm | 1 to 9 mm |
| 4. | Central variegation | Absent | 20 to 30 mm wide band of light green/cream yellow streaks |

BRIEF DESCRIPTION OF THE PHOTOGRAPHS

The accompanying photographs illustrate the overall appearance of the new *Sansevieria* cultivar 'HANSOTI22' showing the colors as true as is reasonably possible with colored reproductions of this type. Colors in the photographs may differ slightly from the color value cited in the detailed botanical description which accurately describe the color of 'HANSOTI22'.

These pictures illustrate the plant form which is the unique characteristic of 'HANSOTI22' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

DETAILED BOTANICAL DESCRIPTION

Figure 1:
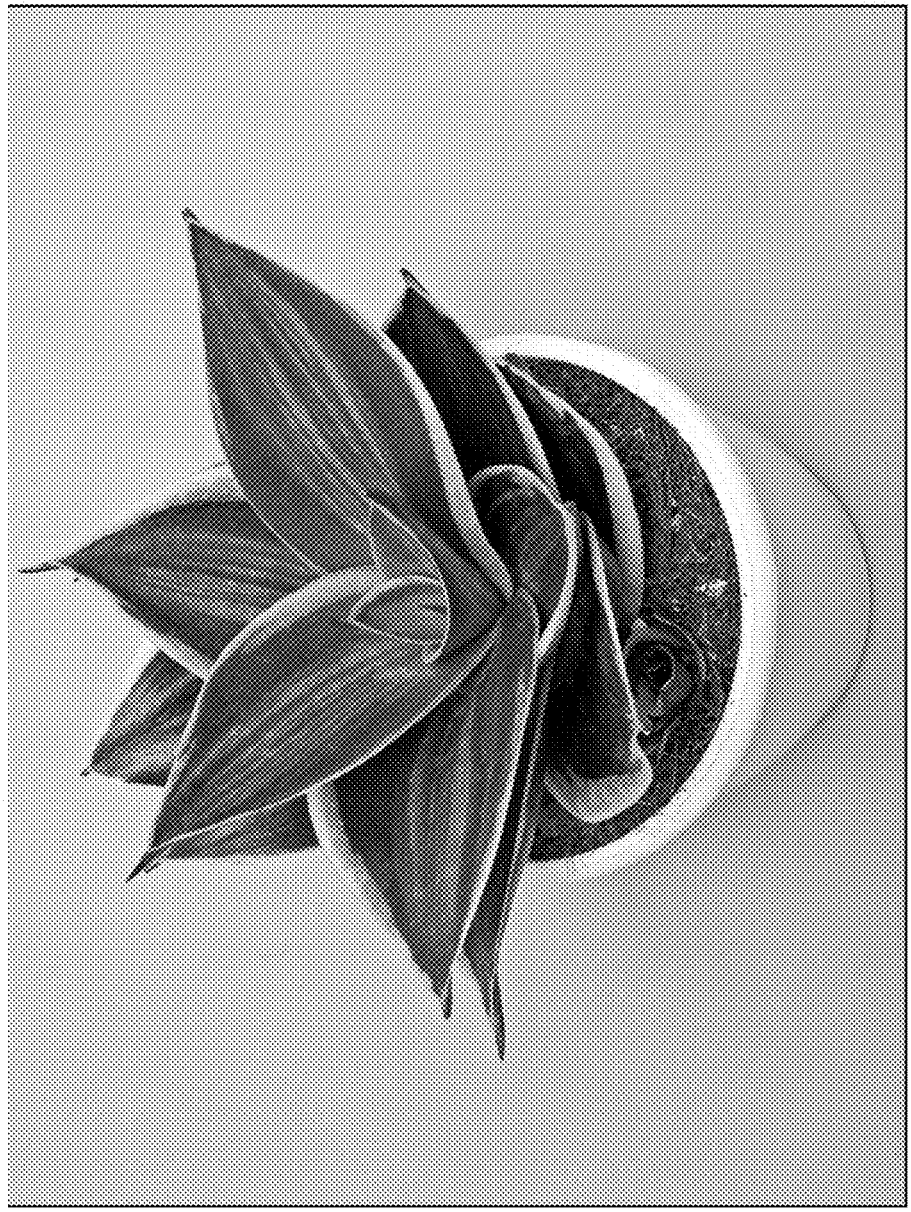
FIG. 1 shows a three-month-old plant of *Sansevieria* 'HANSOTI22' in a 12 cm diameter pot.
Figure 2:
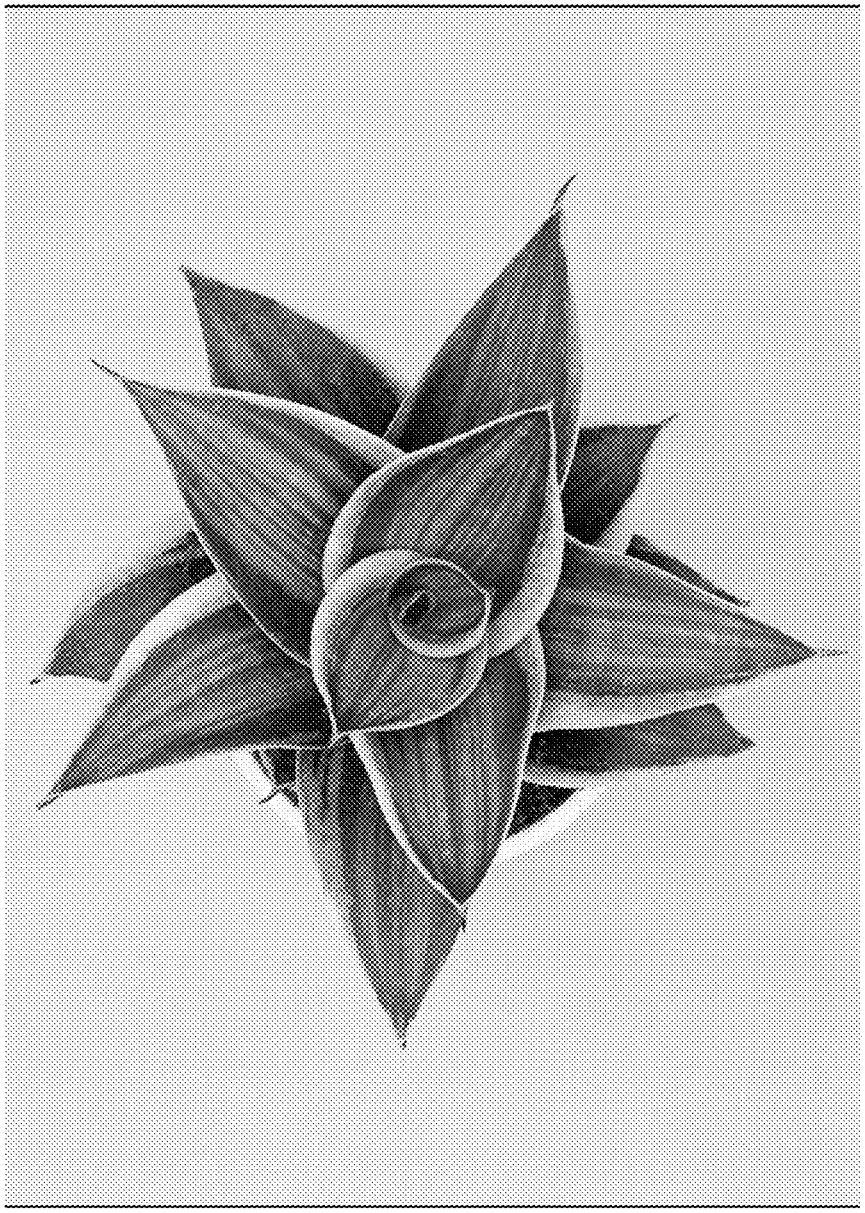
FIG. 2 shows a top view of a plant of 'HANSOTI22'.
Figure 3:
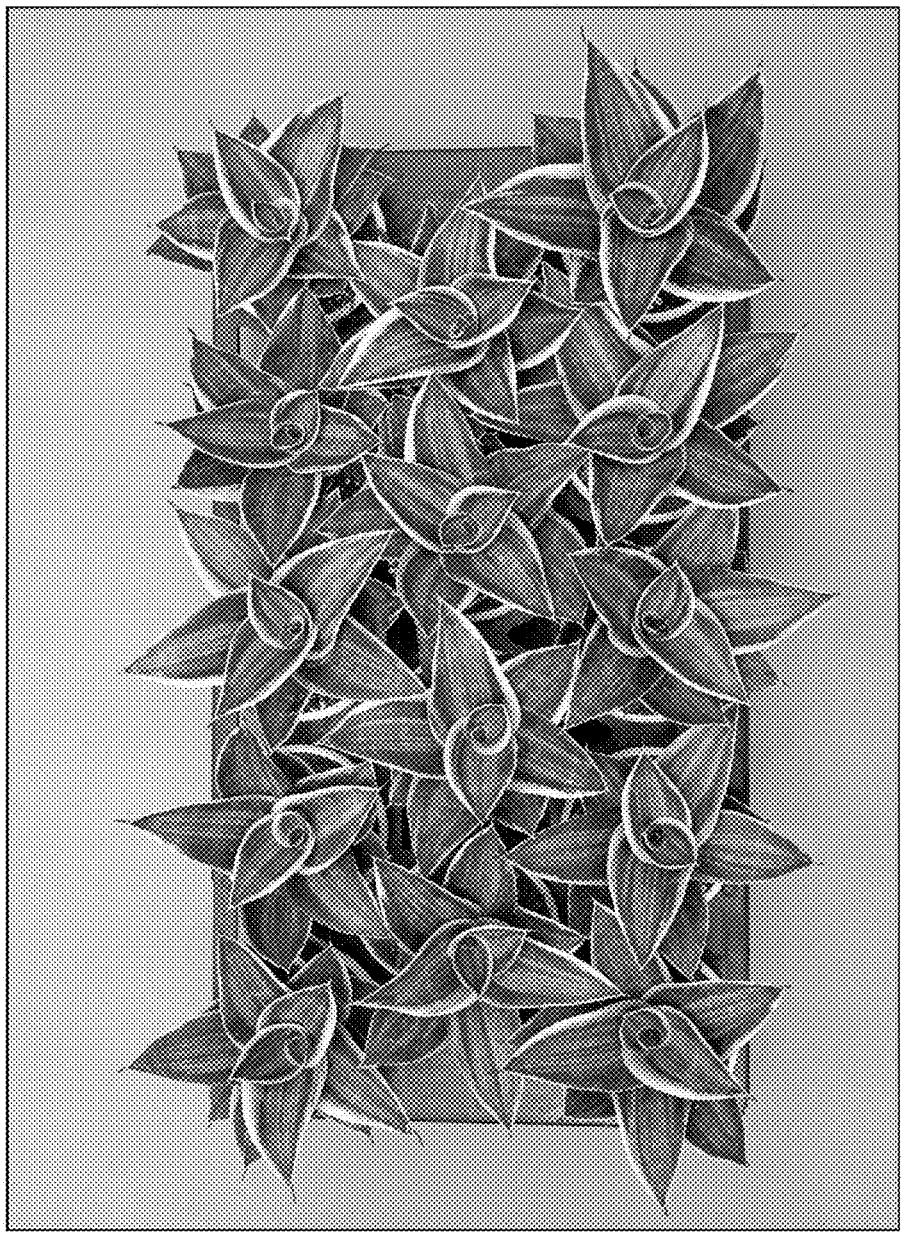
FIG. 3 shows a tray holding 14 'HANSOTI22' plants in 10 cm pots showing uniformity across multiple plants of this new cultivar.
Figure 4:
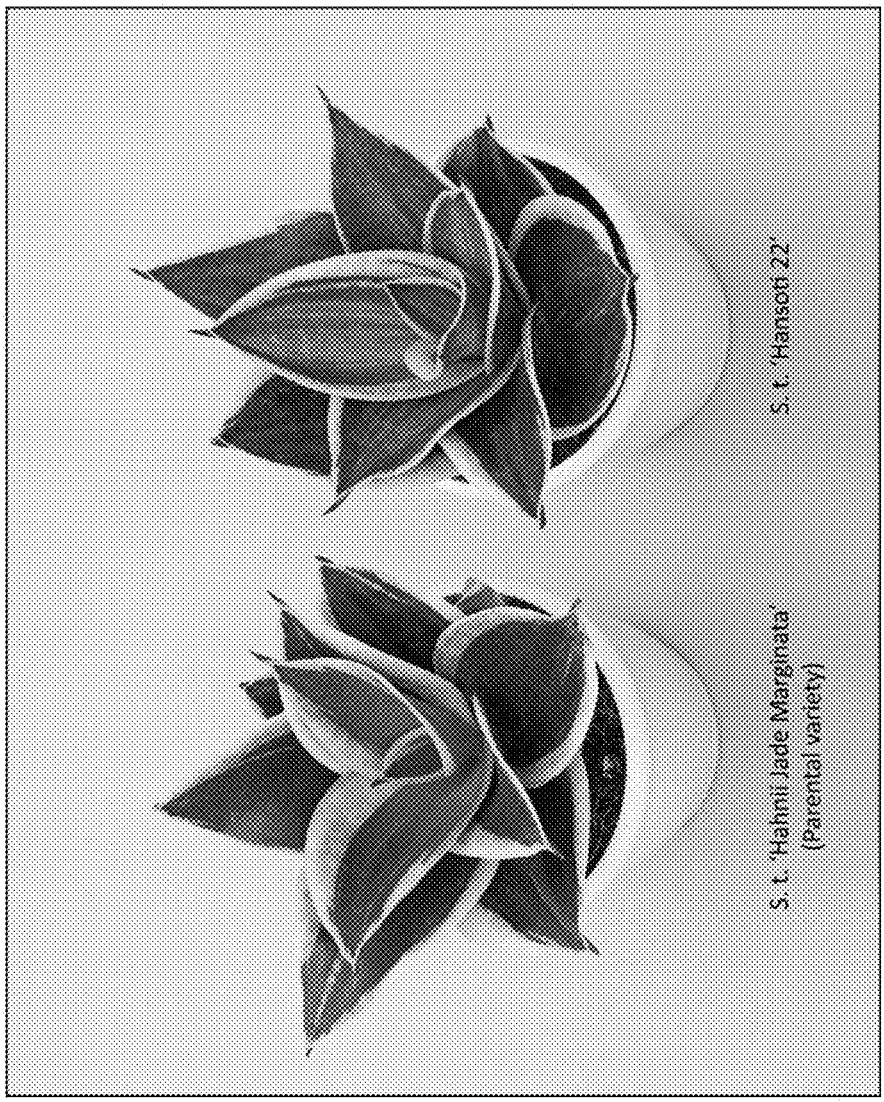
FIG. 4 shows 'HANSOTI22' beside the parent variety *Sansevieria* 'Hahnii Jade Marginata'. The parent plant is on the left, the new variety on the right.
Figure 5:
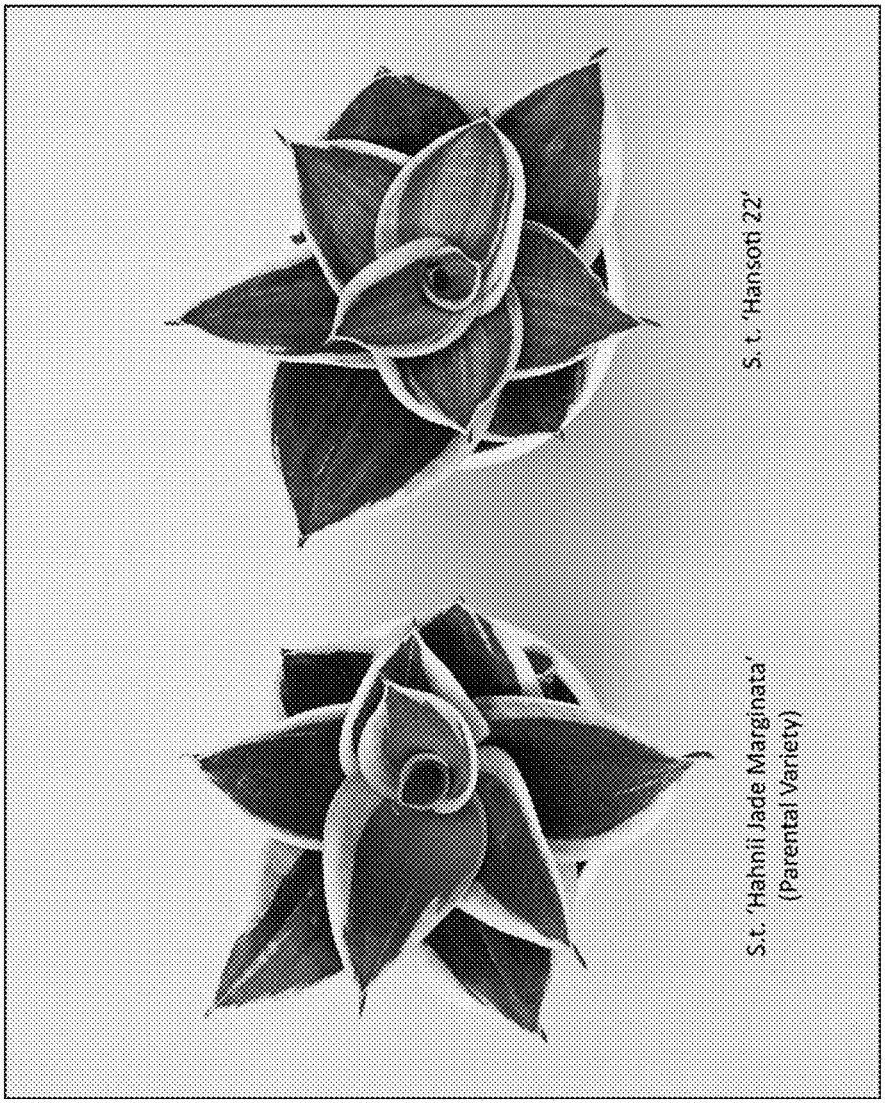
FIG. 5 shows a top view of 'HANSOTI22' beside the parent variety, *Sansevieria* 'Hahnii Jade Marginata'. The parent plant is on the left, the new variety on the right.
Figure 6:
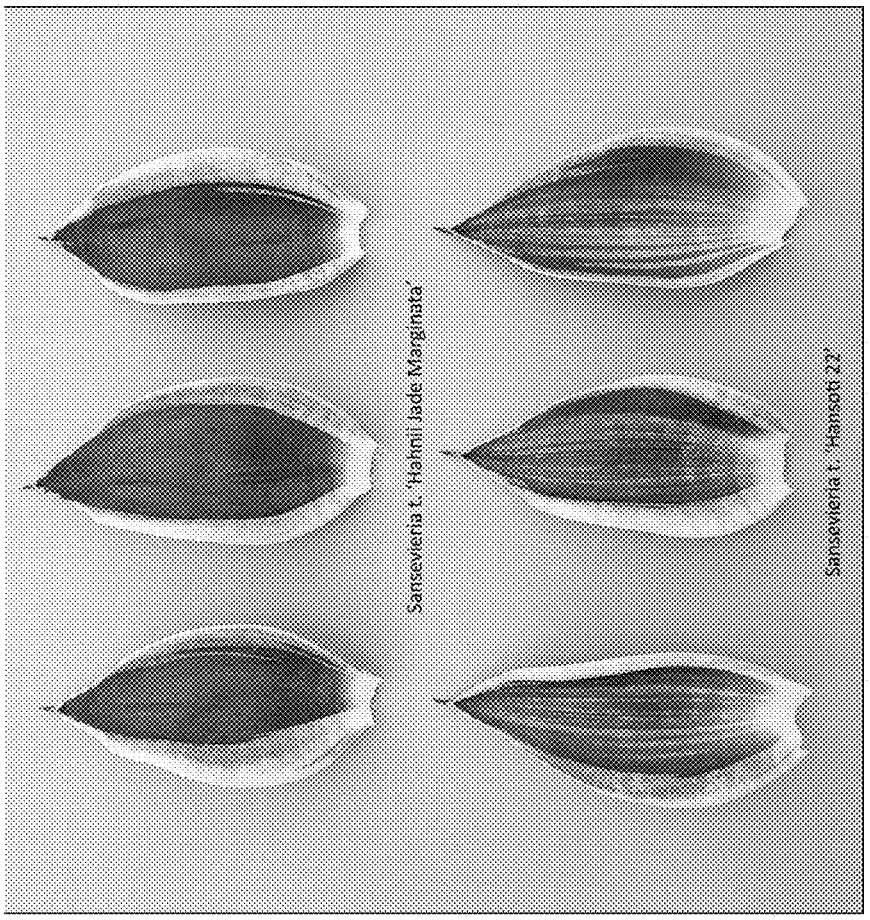
FIG. 6 shows individual leaves of *Sansevieria* 'HANSOTI22' (on bottom) compared to individual leaves of the parent variety *Sansevieria* 'Hahnii Jade Marginata' (on top).

The new *Sansevieria* 'HANSOTI22' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI22' plants grown in an open poly house(high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions).

This crop gets nearly constant fertilization to increase production, Constant Liquid Feed at approximately 150 ppm N, 30 ppm P and 150 ppm K is used along with micronutrients. Production is closely related with proper and complete plant nutrition and an open soilless growing media based on coconut coir. The plants are grown in plastic pots on metal benching in spacing trays Color references are made to The Royal Horticultural Society Colour Chart (R.H.S.), (April 2009) except where general colors of ordinary significance are used.

The photographs and descriptions were taken during the Winter season in Asle, District Satara, Maharashtra State, India when outdoor day temperature was 25° C. to 30° C. The age of the plants described is 3 to 4 months.

Botanical classification: *Sansevieria trifasciata* 'HANSOTI22'.

General information:

*Parentage.*—*Sansevieria trifasciata* 'Hahnii Jade Marginata' (unpatented).

*Optimal growth conditions.*—

*Light intensities.*—High adaptability to outdoor or indoor conditions.

*Temperature.*—Day: 25° C. to 35° C. Night: 12° C. to 25° C.

*Temperature tolerance.*—Tolerant to a low temperature of about 8° C. and a high temperature of 38° C. and above, very heat tolerant.

*Fertilization.*—Constant feed of 150 ppm N, 30 ppm P and 150 ppm K is used along with micronutrients with occasional leaching.

*Growth regulators.*—Not necessary for growth, however rooting hormone aids in rapid and prolific rooting of offsets.

Propagation:

*Typical.*—Side suckers which come true to type.

*Rooting habit and description.*—Rhizomes are elongated, fleshy, giving rise to offsets (side shoots). Offsets root easily with fibrous adventitious roots from cut end. Colored cream to brown, not accurately measured with R.H.S. chart.

*Time to initiate roots.*—15 to 20 days at 25 to 30° C.

*Time to produce a rooted liner.*—About 45 days at 25° C. to 30° C.

*Time to produce a sales ready* 12 *cm potted plant from liner.*—About 3 months at 25° C. to 30° C.

Plant:

*General appearance and form.*—Broad rosette.

*Height.*—About 12 to 15 cm when grown in 12 cm pots.

*Spread.*—About 15 to 17 cm when grown when grown in a 12 cm size container.

*Form.*—Monocot; leaf bases arranged in a rosette around growth point.

*Shape.*—Flat cylindrical.

*Growth rate.*—Moderate.

Foliage:

*Quantity.*—About 9 to 12 in 12 cm, ready to sell plant. Number slowly increases with age and rosette increases in height.

*Arrangement and attachment.*—Single, leaf bases arranged stiffly in a rosette around a central growth point.

*Leaf length.*—About 11 to 13 cm, full mature leaf.

*Leaf width.*—About 5 cm to 8 cm, full mature leaf.

*Overall shape of leaf.*—Broad lanceolate.

*Aspect.*—Slightly upwardly cupped.

*Apex shape.*—Acute, aristate soft tip.

*Base shape.*—Truncate.

*Margin.*—Entire. Entire, sharp, smooth.

*Texture.*—Upper Surface: smooth and waxy texture.

*Texture.*—Under Surface: smooth and waxy texture.

*Pubescence.*—None.

*Color.*—Upper surface mature leaf: Basal dark green colour near Green 139A with cream border near Yellow 4B and central wide band with streaks of Yellow-Green N144C and N144D. Lower surface mature leaf: Basal dark green colour near Green 139A with cream border near Yellow 4B and faint central wide band with streaks of Yellow-Green N144C and N144D.

*Margin coloration.*—Near RHS Yellow 4B, upper and lower surfaces.

*Venation.*—Pattern: Longitudinal/parallel leaf shape.

*Venation color.*—Indistinguishable from leaf blade.

*Leaf fragrance.*—None.

Other:

*Inflorescence description.*—Flowers not observed to date.

*Weather resistance.*—Moderately drought tolerant.

*Pest resistance.*—Reasonably resistant to pests, susceptible to root mealybugs.

*Disease resistance.*—Occasionally shows Anthracnose and leaf spots but largely disease free from clean mother stock.

*Fruit/seed production.*—No fruits/seeds detected to date.

What is claimed is:

1. A new and distinct cultivar of *Sansevieria* plant named 'HANSOTI22' as herein illustrated and described.

* * * * *